(12) United States Patent
Odidi et al.

(10) Patent No.: US 7,906,143 B1
(45) Date of Patent: *Mar. 15, 2011

(54) CONTROLLED RELEASE PHARMACEUTICAL DELIVERY DEVICE AND PROCESS FOR PREPARATION THEREOF

(76) Inventors: Isa Odidi, Mississauga (CA); Amina Odidi, Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/166,701

(22) Filed: Oct. 5, 1998

(51) Int. Cl.
*A61K 9/14* (2006.01)
*A61K 9/22* (2006.01)
*A61F 2/00* (2006.01)

(52) U.S. Cl. .................. 424/488; 424/425; 424/468

(58) Field of Classification Search .......... 424/449–500, 424/425
See application file for complete search history.

(56) References Cited

U.S. PATENT DOCUMENTS

| | | | |
|---|---|---|---|
| 3,789,117 A * | 1/1974 | Tsujino | |
| 3,845,770 A | 11/1974 | Theeuwes et al. | 128/260 |
| 3,916,899 A | 11/1975 | Theeuwes et al. | 128/260 |
| 4,016,880 A | 4/1977 | Theeuwes et al. | 128/260 |
| 4,160,452 A | 7/1979 | Theeuwes | 128/260 |
| 4,200,098 A | 4/1980 | Ayer et al. | 128/260 |
| 4,218,433 A * | 8/1980 | Kooichi et al. | 424/467 |
| 4,252,786 A * | 2/1981 | Weiss et al. | 424/495 |
| 4,309,405 A * | 1/1982 | Guley et al. | |
| 4,610,870 A * | 9/1986 | Jain et al. | |
| 4,666,705 A * | 5/1987 | DeCrosta et al. | |
| 4,940,587 A * | 7/1990 | Jenkins et al. | 424/480 |
| 6,210,710 B1 * | 4/2001 | Skinner | |

OTHER PUBLICATIONS

Steward 1995 Review of Pharmaceutical Controlled Release Method and Devices 12 pages.*

* cited by examiner

*Primary Examiner* — Brandon J Fetterolf
*Assistant Examiner* — Shirley V Gembeh

(57) ABSTRACT

The present invention relates to a controlled release pharmaceutical delivery device which provides sustained or pulsatile delivery of a selected pharmaceutically active substance for a predetermined period of time. The device comprises about 1 to 80% by weight covalently crosslinked water insoluble, water-swellable polymers and about 1 to 75% by weight uncrosslinked, linear water soluble polymers.

The invention also provides pharmaceutical compositions and methods for making such compositions in which a pharmaceutically active agent is incorporated into the delivery device.

13 Claims, No Drawings

CONTROLLED RELEASE PHARMACEUTICAL DELIVERY DEVICE AND PROCESS FOR PREPARATION THEREOF

FIELD OF THE INVENTION

The present invention relates to a controlled release device which provides sustained or pulsatile delivery of pharmaceutically active substances for a predetermined period of time. This invention further relates to a process for the manufacture of such a device and pharmaceutical compositions including the same.

DESCRIPTION OF THE BACKGROUND

Different systems have been developed for the delivery of pharmaceutical agents. One such system operates by means of a complicated osmotic pumping mechanism which is expensive and often difficult to prepare. Also known are delivery devices made of matrices using hydrogels. These devices use one or more hydrogels either selected from uncrosslinked linear polymers or from crosslinked polymers. None use both types of polymers in a single device.

While these systems do act to deliver selected pharmaceuticals, they do not provide for controlled release of the pharmaceutical in a sustained or pulsatile mariner for a predetermined period of time. In devices using uncrosslinked polymers, viscosity is the rate controlling factor for drug release kinetics. In these systems a gelatinous layer is formed on the surface upon hydration. The thickness and durability of this gelatinous layer depends upon the concentration, as well as the molecular weight and viscosity of the polymer in the device. At higher concentrations the linear polymer chains entangle to a greater degree leading to virtual crosslinking and a stronger gel layer. Drug release is effected by the dissolution of the polymer and erosion of the gel layer. Hence the rate of erosion controls the release rate.

In the case of devices using covalently crosslinked polymers, the drug is trapped in a glassy core in the dry state. On contact with an aqueous medium the surface of the device is hydrated to form a gelatinous layer which is different from the gel layer seen in uncrosslinked linear polymers. The hydrogel formed by crosslinked polymers does not consist of entangled chains but discrete microgels made up of many polymer particles, called a crosslinked network, in which the drug is dispersed. Therefore drug is trapped in the hydrogel domains. These hydrogels are not water soluble and do not dissolve, thus erosion as seen in uncrosslinked linear polymers does not occur. Drug release is by the osmotic pressure generated within the fully hydrated hydrogel which works to break up the structure by sloughing off discrete pieces of the hydrogel. The hydrogels remain intact while drug continues to diffuse through the gel layer at uniform rate.

U.S. Pat. Nos. 3,845,770, 3,916,899, 4,016,880, 4,160,452 and 4,200,098 disclose such delivery systems as described above. However, none of these patents teach the use of both covalently, crosslinked and uncrosslinked linear polymers in combination in a single delivery device for the controlled or pulsatile delivery of pharmaceutically active agents thereby taking advantage of their unique but different properties and mechanism of drug release.

SUMMARY OF THE INVENTION

The present invention provides a unique and novel synergistic approach to the use of multiple and differing polymers for modulating drug delivery.

It is an object of the present invention to provide a controlled release device which delivers therapeutically effective amounts of pharmaceutically active agents for a predetermined period of time in a controlled, continuous or pulsatile manner in mammals, especially human beings.

In accordance with an aspect of the invention is a controlled release pharmaceutical delivery device which provides sustained or pulsatile delivery of a selected pharmaceutically active substance for a predetermined period of time, the device comprises;
 about 1 to 80% by weight covalently crosslinked water insoluble, water-swellable polymers; and
 about 1 to 75% by weight uncrosslinked, linear water soluble polymers.

In accordance with another aspect of the present invention is a controlled release pharmaceutical delivery device which provides sustained or pulsatile delivery of a selected pharmaceutically active substance for a predetermined period of time, the device comprises;
 about 1 to 60% by weight of hydroxyethylcellulose;
 about 1 to 75% by weight of hydroxypropylmethyl cellulose;
 about 1 to 60% by weight of ethylcellulose;
 about 1 to 80% by weight of at least one Carbopol® resin;
 about less than 10% by weight of talc;
 about less than 10% by weight of magnesium stearate; and
 about less than 95% by weight granulating and tableting aids.

In accordance with yet another aspect of the present invention is a method for making an extended release formulation of pharmaceutically active agents, the method comprises;
 blending about 1 to 80% pharmaceutically active agent with about 1 to 80% by weight covalently crosslinked water insoluble, water swellable polymers, and about 1 to 75% by weight uncrosslinked, linear water soluble polymers.

In accordance with another aspect of the present invention is a method for making an extended release formulation of pharmaceutically active agents, the method comprises;
 blending about 1 to 80% pharmaceutically active agent with about 1 to 70% by weight uncrosslinked, water soluble polymers to form a homogeneous blend;
 granulating said homogeneous blend with a granulating solution to form a wet mass of granules and kneading said wet mass;
 drying said wet granules to a loss on drying of about less than 5%;
 reducing said dried granules such that granule size is less than about 1400 microns;
 blending said milled granules with about 1 to 80% of a crosslinked polymer, about less than 5% of a glidant, and about less than 5% of a lubricant; and
 compressing the lubricated granules into tablets.

In accordance with yet another aspect of the present invention is a pharmaceutical composition which comprises;
 about 1 to 80% by weight pharmaceutically active agent;
 about 1 to 80% by weight covalently crosslinked water insoluble water swellable polymers; and
 about 1 to 75% by weight uncrosslinked, linear water soluble polymers.

In accordance with yet another aspect of the present invention is a pharmaceutical composition which comprises:
 about 1 to 80% pharmaceutically active agent;
 about 1 to 60% by weight of hydroxyethylcellulose;
 about 1 to 75% by weight of hydroxypropylmethyl cellulose;
 about 1 to 60% by weight of ethylcellulose;

about 1 to 80% by weight of at least one Carbopol® resin;
about less than 10% by weight of talc;
about less than 10% by weight of magnesium stearate; and
about less than 95% by weight granulating and tableting aids.

In a further aspect of this invention there is provided a method for delivering soluble or poorly soluble pharmaceutically active agents by deliberate manipulation of the composition and ratios of crosslinked and uncrosslinked polymers present in the device.

In yet another aspect of this invention the controlled release delivery device also has use in other applications in which the release of a substance is desired into an environment which eventually comes into contact with fluids.

DETAILED DESCRIPTION OF THE PREFERRED EMBODIMENTS

The novel controlled delivery device of the present invention provides a composition and a process for the formulation of pharmaceutically active agents into sustained release matrix tablets. The present invention is simple to prepare and permits efficient and reproducible mass production of the device using conventional pharmaceutical and biochemistry techniques.

Uncrosslinked linear polymers suitable for use in the present invention are the cellulosics preferably hydroxyethyl cellulose (HEC), hydroxypropylmethyl cellulose, ethylcellulose and hydroxypropyl cellulose. Crosslinked polymer suitable for use in the present invention are polymers of acrylic acid crosslinked with polyalkenyl alcohols or divinyl glycol. For example, these include water-swellable, high-molecular-weight crosslinked homopolymers and copolymers of acrylic acid, most preferably Carbopol resins.

In the preferred form the sustained release device of the present invention is presented as a matrix tablet suitable for oral administration which is prepared by intimately blending about 1 to 80% of a selected pharmaceutically active agent(s) with about 1 to 60% of an uncrosslinked linear polymer such as hydroxyethylcellulose (preferably Natrosol® 25OHHX PHARM) and about 1 to 75% of another uncrosslinked polymer such as hydroxypropylmethyl cellulose (preferably Methocel® premium grade type K100M CR) in a planetary or high shear mixer until a homogeneous mixture is formed. The homogeneous mixture is then granulated with a granulating solution (preferably isopropyl alcohol) in a planetary or high shear mixer. It is preferable to knead the resultant wet mass for 1-3 minutes after wet granulation. The wet granules are then dried in a fluid bed dryer or tray dryer to a loss on drying (LOD) of about <5%. Preferably, the granules are dried in a tray dryer at >40° C. to an LOD of about <2%.

The dried granules are size reduced in a mill, preferably a Cone mill, such that the resultant granule size is about <2000 microns. The milled granules are intimately blended with about 1 to 80% by weight of a crosslinked polymer such as Carbopol® resin, preferably Carbopol® 934 P NF or 971 P NF in a V-blender. The Carbopol® treated granules are then intimately blended with a glidant such as talc (about <5% by weight) in a V-blender. The talc treated granules are then intimately blended with a lubricant such as magnesium stearate (about <5% by weight) in a V-blender. Finally, compression of the lubricated granules is done using a rotary tablet press to form tablets suitable for oral administration. The resultant tablets have a hardness of about >3 Strong Cobb units and a friability of about <1%.

The device may contain up to 95% by weight other granulating or tableting aids such as silicone dioxide, lactose, microcrystalline cellulose, calcium phosphate and mannitol.

The conditions under which the materials are processed and the relative proportions of the several components produces a device and composition having unique sustained release characteristics. The sustained release characteristic of the composition can be predetermined and varied by adjusting the makeup of the composition within the aforesaid limits. The duration, uniformity and continuity of release of the pharmaceutically active agent(s) can be suitably controlled by varying the relative amount of the covalently crosslinked and uncrosslinked linear polymers.

The finished tablet may be film coated with about 0.5 to 50% by weight of a suitable film coating comprising anionic polymers based on methacrylic acid and methacrylic acid esters or neutral methacrylic acid esters with a small proportion of trimethylammonioethyl methacrylate chloride or cellulose esters.

The pharmaceutically active agents that may be used with the device and in the compositions of the present invention may include but are not limited to diltiazem, buspirone, tramadol, gabapentin, verapamil, etodolac, naproxen, diclofenac, COX2 inhibitors, budesonide, venlafaxine, metoprolol, carbidopa, levodopa, carbamazepine, ibuprofen, morphine, pseudoephedrine, paracetamol, cisapride, pilocarpine, to methylphenidine, nifedipine, nicardipine, felodipine, captropril, terfenadine, pentoxifylline, fenofibrate, flipizide, aciclovir, zidovudine, moclobemide, potassium chloride, lamotrigine, citalopram, cladribine, loratadine, pancrelipase, lithium carbonate, orphenadrine, ketoprofen, procainamide, ferrous sulfate, risperidone, clonazepam, nefazodone, lovastatin, simvastatin, pravachol, ketorolac, hydromorphone, ticlopidine, seligiline, alprazolam, divalproex or phenytoin.

When the delivery device of this invention is made as a composition containing a pharmaceutical agent and is administered to the gastrointestinal tract by the oral route, it comes into contact with an aqueous environment and hydrates forming a gelatinous layer. If the drug is poorly soluble it will partition into the hydrophobic domains of the device provided by the crosslinked polymer while some will be entrapped in the hydrophilic matrix provided especially by the uncrosslinked polymer. This results in dependency $\sqrt{t}$(Fickian) and zero order (case II) drug dissolution kinetics. For water soluble drugs, Fickian drug release kinetics will occur due to fast dissolution of the drug through the water filled interstitial spaces between microgels of the crosslinked polymer and dissolution and erosion of the uncrosslinked polymer. The presence of the crosslinked polymer, which does not dissolve, helps to maintain the integrity of the swollen gel structure that results. The mechanism or mechanisms that dominate will depend upon the ratio of crosslinked and uncrosslinked polymers present in the device which in turn impacts on the macro- and microviscosities of the gel layer. Thus, manipulation of the ratios of uncrosslinked and crosslinked polymers, results either in the controlled, sustained release or pulsatile release of the pharmaceutical contained therein.

EXAMPLES

The examples are described for the purposes of illustration and are not intended to limit the scope of the invention.

Methods of chemistry, biochemistry and pharmacology referred to but not explicitly described in this disclosure and examples are reported in the scientific literature and are well known to those skilled in the art. Matrix tablets are produced according to the process previously outlined in the detailed description of the preferred embodiments;

Example 1

Diltiazem hydrochloride ER tablets

|  | % composition |
|---|---|
| Diltiazem hydrochloride | 30 |
| Natrosol 250 HHX | 25 |
| Carbopol 934P | 10 |
| Hydroxypropylmethyl cellulose K100M CR | 33 |
| Talc | 1 |
| Magnesium stearate | 1 |

Diltiazem hydrochloride was blended with Natrosol and hydroxypropylmethyl cellulose in a high shear mixer until a homogeneous mixture was obtained. The mixture was granulated with isopropyl alcohol and dried in fluid bed dryer to a loss on drying of 1.5%. The dried granules were then passed through a sieve #14 mesh. The milled granules were blended with Carbopol, talc and magnesium stearate in a V-blender. Finally, the treated granules were pressed into tablets using a rotary tablet press.

Example 2

Tramadol ER tablets

|  | % composition |
|---|---|
| Tramadol | 40 |
| Natrosol 250 HHX | 15 |
| Carbopol 934P | 8 |
| Hydroxypropylmethyl cellulose K100M CR | 35 |
| Talc | 1 |
| Magnesium stearate | 1 |

Tramadol was blended with Natrosol and hydroxypropylmethyl cellulose in a high shear mixer until a homogeneous mixture was obtained. The mixture was granulated with isopropyl alcohol and dried in fluid bed dryer to a loss on drying of 1.5%. The dried granules were passed through a sieve #14 mesh. The milled granules were blended with Carbopol, talc and magnesium stearate in a V-blender. Finally, the treated granules were pressed into tablets using a rotary tablet press.

Example 3

Buspirone ER tablet

|  | % composition |
|---|---|
| Buspirone hydrochloride | 2.5 |
| Natrosol 250 HHX | 20 |
| Lactose | 17.5 |
| Silicone dioxide | 1 |
| Carbopol 934P | 10 |
| Hydroxypropylmethyl cellulose K 100M CR | 35 |
| Ethylcellulose | 5 |
| Microcrystalline cellulose | 7 |
| Talc | 1 |

The Buspirone was dissolved in isopropyl alcohol. Lactose was blended with Natrosol, ethylcellulose, microcrystalline cellulose, silicone dioxide and hydroxypropylmethyl cellulose in a high shear mixer until a homogeneous mixture was obtained. This mixture was granulated with the isopropyl alcohol Buspirone hydrochloride solution and dried in fluid bed dryer to a loss on drying of 1.5%. The dried granules were passed through a sieve #14 mesh. The milled granules were blended with Carbopol, talc and magnesium stearate in a V-blender. Finally, the treated granules were pressed into tablets using a rotary tablet press.

Although preferred embodiments of the invention have been described herein in detail, it is understood by those skilled in the art that variations may be made thereto without departing from the spirit of the invention of the scope of the appended claims.

The invention claimed is:

1. A controlled release pharmaceutical delivery composition which provides sustained delivery of a pharmaceutically active substance for a predetermined period of time, said composition comprising;
   about 1-80% by weight polymers of acrylic acid crosslinked with polyalkenyl alcohols or divinyl alcohol;
   about 1% to 58% by weight of a mixture of hydroxyethyl cellulose and hydroxypropyl methylcellulose;
   about less than 10% by weight talc;
   about less than 10% by weight magnesium stearate; and
   about 1-80% by weight of a pharmaceutically active agent;
   wherein said acrylic acid crosslinked polymers, hydroxyethyl cellulose and hydroxypropyl methylcellulose, talc, magnesium stearate and pharmaceutically active agent are provided as a homogenous mixture.

2. The composition of claim 1, wherein said polymers of acrylic acid crosslinked with polyalkenyl alcohols or divinyl alcohol are water-swellable and high-molecular-weight polymers.

3. The composition of claim 1, wherein said composition is film coated with about 0.5 to 50% by weight of a coating material comprising anionic polymers based on methacrylic acid and methacrylic acid esters or neutral methacrylic acid esters with trimethylammonioethyl methacrylate chloride or cellulose esters.

4. The composition of claim 1, wherein said composition additionally comprises about less than 95% by weight granulating and tableting aids.

5. A controlled release pharmaceutical delivery composition which provides sustained delivery of a pharmaceutically active substance for a predetermined period of time, said composition comprising;
   about 1% to 58% by weight of a mixture of hydroxyethylcellulose and hydroxypropylmethyl cellulose;
   about 1 to 60% by weight of ethylcellulose;
   about 1 to 80% by weight of at least one water-swellable, high-molecular-weight acrylic acid polymer crosslinked with polyalkenyl alcohols or divinyl alcohol;
   about less 10% by weight of talc;
   about less than 10% by weight of magnesium stearate;
   about less than 95% by weight granulating and tableting aids; and
   about 1-80% of a pharmaceutically active agent,
   wherein said hydroxyethylcellulose, hydroxypropylmethyl cellulose, ethylcellulose, acrylic acid polymer, talc, magnesium stearate, granulating and tableting aid, and pharmaceutically active agent are provided as a matrix.

6. The composition of claim 5, wherein said pharmaceutically active agent is selected from the group consisting of naproxen, COX2 inhibitors, budesonide, venlafaxine, metoprolol, carbidopa, levodopa, carbamazepine, ibuprofen, morphine, pseudoephedrine, paracetamol, cisapride, pilocarpine, methylphenidine, nicardipine, felodipine, captropril, terfenadine, fenofibrate, aciclovir, zidovudine, moclobemide, potassium chloride, lamotrigine, cladribine, loratadine, pancrelipase, lithium carbonate, orphenadrine, procainamide, ferrous sulfate, risperidone, clonazepam, lovastatin, simvastatin, pravachol, ketorolac, hydromorphone, ticlopidine, seligiline, alprazolam, divalproex and phenytoin.

7. The composition as claimed in claim 1 wherein, said composition additionally comprises one or more pharmaceutical excipients selected from the group consisting of lactose, silicone dioxide, sodium lauryl sulphate, calcium phosphate, calcium sulphate, silicified microcrystalline cellulose, Gelucire® and Compritol®.

8. A pharmaceutical composition comprising;
   about 1 to 80% by weight pharmaceutically active agent;
   about 1 to 80% by weight of polymers of acrylic acid crosslinked with polyalkenyl alcohols or divinyl alcohol; and
   about 1% to 58% by weight of a mixture of hydroxyethyl cellulose and hydroxypropyl methylcellulose; wherein said polymers of acrylic acid, hydroxyethyl cellulose and hydroxypropyl methyl cellulose, and pharmaceutically active agent are provided as a homogenous mixture.

9. The composition of claim 8, wherein said composition is film coated with about 0.5 to 50% by weight of a pharmaceutically acceptable film coating comprising anionic polymers based on methacrylic acid and methacrylic acid esters or neutral methacrylic acid esters with trimethylammonioethyl methacrylate chloride or cellulose esters.

10. The composition of claim 8, wherein said pharmaceutically active agent is selected from the group consisting of naproxen, COX2 inhibitors, budesonide, venlafaxine, metoprolol, carbidopa, levodopa, carbamazepine, ibuprofen, morphine, pseudoephedrine, paracetamol, cisapride, pilocarpine, methylphenidine, nicardipine, felodipine, captropril, terfenadine, fenofibrate, aciclovir, zidovudine, moclobemide, potassium chloride, lamotrigine, cladribine, loratadine, pancrelipase, lithium carbonate, orphenadrine, procainamide, ferrous sulfate, risperidone, clonazepam, lovastatin, simvastatin, pravachol, ketorolac, hydromorphone, ticlopidine, seligiline, alprazolam, divalproex and phenytoin.

11. A pharmaceutical composition comprising:
    about 1 to 80% pharmaceutically active agent;
    about 1% to 58% by weight of hydroxyethylcellulose and hydroxypropylmethyl cellulose;
    about 1 to 60% by weight of ethylcellulose;
    about 1 to 80% by weight of at least one water-swellable, high-molecular-weight acrylic acid polymer crosslinked with polyalkenyl alcohols or divinyl alcohol;
    about less than 10% by weight of talc;
    about less than 10% by weight of magnesium stearate; and
    about less than 95% by weight granulating and tableting aids, wherein said pharmaceutically active agent, hydroxyethyl cellulose and hydroxypropyl methylcellulose, ethylcellulose, talc, magnesium stearate, and granulating and tableting aids, are provided as a homogenous mixture.

12. The composition of claim 11, wherein said tableting and granulating aids are selected from the group consisting of silicone dioxide, lactose, microcrystalline cellulose, calcium phosphate and mannitol.

13. A pharmaceutical composition comprising;
    about 1 to 80% by weight pharmaceutically active agent;
    about 1 to 80% by weight of polymers of acrylic acid crosslinked with polyalkenyl alcohols or divinyl alcohol;
    about 1% to 58% by weight of a mixture of hydroxyethyl cellulose and hydroxypropyl methylcellulose; wherein said polymers of acrylic acid, hydroxyethyl cellulose and hydroxypropyl methylcellulose and the pharmaceutically active agent are provided as a homogenous mixture; and
    about 0.5 to 50% by weight of a coating material coating said matrix, said coating material comprising anionic polymers based on methacrylic acid and methacrylic acid esters or neutral methacrylic acid esters with trimethylammonioethyl methacrylate chloride or cellulose esters.

* * * * *

UNITED STATES PATENT AND TRADEMARK OFFICE
CERTIFICATE OF CORRECTION

| | | |
|---|---|---|
| PATENT NO. | : 7,906,143 B1 | Page 1 of 1 |
| APPLICATION NO. | : 09/166701 | |
| DATED | : March 15, 2011 | |
| INVENTOR(S) | : Isa Odidi et al. | |

It is certified that error appears in the above-identified patent and that said Letters Patent is hereby corrected as shown below:

On the title page, item #73 assignee should read:

INTELLIPHARMACEUTICS CORP.

Signed and Sealed this
Twentieth Day of September, 2011

David J. Kappos
*Director of the United States Patent and Trademark Office*